United States Patent [19]

Huang et al.

[11] Patent Number: 4,874,745

[45] Date of Patent: Oct. 17, 1989

[54] RENIN-INHIBITORY PEPSTATIN PHENYL DERIVATIVES

[75] Inventors: Leeyuan Huang, Watchung; Lawrence Koupal, Colonia; Joseph Dunn, Jr., Parlin; Jerrold M. Liesch, Princeton Junction; Otto Hensens, Red Bank; H. Boyd Woodruff, Watchung, all of N.J.

[73] Assignee: Merck & Co., Inc., Rahway, N.J.

[21] Appl. No.: 103,324

[22] Filed: Oct. 1, 1987

[51] Int. Cl.$^4$ .................. H61K 37/43; C07K 5/10
[52] U.S. Cl. ........................... 514/18; 530/330; 530/332
[58] Field of Search ................. 514/18; 530/330, 332

[56] References Cited

U.S. PATENT DOCUMENTS 4,746,648  5/1988  Wagnon et al. ................ 530/332

OTHER PUBLICATIONS

The Journal of Antibiotics, 1975, pp. 1016–1017, vol. 28, No. 12.

*Primary Examiner*—Delbert R. Phillips
*Attorney, Agent, or Firm*—Richard A. Elder; Frank Chow; Hesna Pfeiffer

[57] ABSTRACT

A phenyl derivative of pepstatin A, which is much more potent than pepstatin in inhibiting renin enzyme activity and has significantly greater selectivity for renin over pepsin inhibition than does pepstatin, which is useful in treating hypertension and congestive heart failure.

6 Claims, No Drawings

RENIN-INHIBITORY PEPSTATIN PHENYL DERIVATIVES

The present invention is concerned with a novel pepstatin phenyl derivative of the formula, $C_{40}H_{59}N_5O_9$, which selectively inhibits the proteolytic enzyme, renin, and is a useful starting material for the preparation of statine and the benzyl analog of statine; with pharmaceutical compositions containing the novel compound of the present invention as an active ingredient; and with methods of treating hypertension and congestive heart failure and methods of diagnosis which utilize the novel compound of the present invention.

BACKGROUND OF THE INVENTION

Renin is an endopeptidase secreted by the juxtaglomerular cells of the kidney, which cleaves its plasma substrate, angiotensinogen, specifically at the 10-11 peptide bond, i.e., between Leu 10 and Leu 11 in the equinine substrate, as described by Skeggs et al, *J. Exper. Med.* 1957, 106, 439, or between the Leu 10 and Val 11 in the human renin substrate, as elucidated by Tewksbury et al., *Circulation* 59, 60, Supp. II: 132, Oct. 1979. Renin cleaves angiotensinogen to split off the decapeptide, angiotensin I, which is converted by angiotensin-converting enzyme to the potent pressor substance angiotensin II. Thus, the renin-angiotensin system plays an important role in normal cardiovascular homeostasis and in some forms of hypertension.

Inhibitors of angiotensin I converting enzyme have proven useful in the modulation of the renin-angiotensin system and consequently, specific inhibitors of the limiting enzymatic step that ultimately regulates angiotensin II production, the action of renin on its substrate, have also been sought as effective investigative tools and as therapeutic agents in the treatment of hypertension and congestive heart failure.

Renin antibody, pepstatin, phospholipids, and substrate analogs, including tetrapeptides and octa-toz8 tridecapeptides, with inhibition constants ($K_i$) in the $10^{-3}$ to $10^{-6}$M region, have been studied.

Many efforts have been made to prepare a specific renin inhibitor based on pig renin substrate analogy, which as been shown to correlate well with and predict human renin inhibitor activity. The octapeptide amino acid sequence extending from histidine-6 through tyrosine-13

```
        6   7   8   9   10  11  12  13
      (—His—Pro—Phe—His—Leu—Leu—Val—Tyr—)
``` has been shown to have kinetic parameters essentially the same as those of the full tetradecapeptide renin substrate.

Kokubu et al., *Biochem. Pharmacol.*, 22, 3217-3223, 1973, synthesized a number of analogs of the tetrapeptide found between residues 10 to 13, but while inhibition could be shown, inhibitory constants were only of the order of $10^{-3}$M. Analogs of a larger segment of renin substrate were synthesized, Burton et al., *Biochemistry* 14: 3892-3898, 1975, and Poulsen et al., *Biochemistry* 12: 3877-3882, 1973, but a lack of solubility and weak binding (large inhibitory constant) have proven to be major obstacles to obtaining effective renin inhibitors.

In the case of pepstatin, Umezawa et al., in *J. Antibiot.* (Tokyo) 23: 259-262, 1970, reported the isolated (from culture filtrates of actinomyces) of that N-acylated pentapeptide, (pepstatin), having the structure:

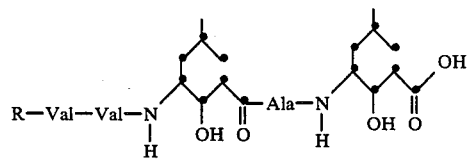

This pentapeptide was reported to be an inhibitor of aspartyl proteases such as pepsin, cathepsin D, and renin, with an $I_{50}$ ratio against pepsin and renin generally in the range of 300 to 1000, depending on the sensitivity of the assay. Gross et al., *Science* 175:656, 1972, reported that pepstatin reduces blood pressure in vivo after the injection of hog renin into nephrectomized rats, but pepstatin has not found very wide application as an experimental agent because of its limited solubility and its inhibition of a variety of other acid proteases in addition to renin.

It has now been found that a novel phenyl derivative of pepstatin is about four times more potent than pepstatin A in inhibiting renin activity and has an $I_{50}$ ratio of renin to pepsin which is about ten-fold less than that for pepstatin A. This new phenyl derivative, therefore, offers significant therapeutic advantages for the treatment of high blood pressure and congestive heart failure in mammals. This derivative is also a useful starting material for the preparation of statine, a synthetic amino acid, which has been successfully substituted into renin substrates as a peptide bond isostere at the 10-11 position.

DESCRIPTION OF THE INVENTION

The present invention discloses a new renin-inhibitory pepstatin derivative of the formula:

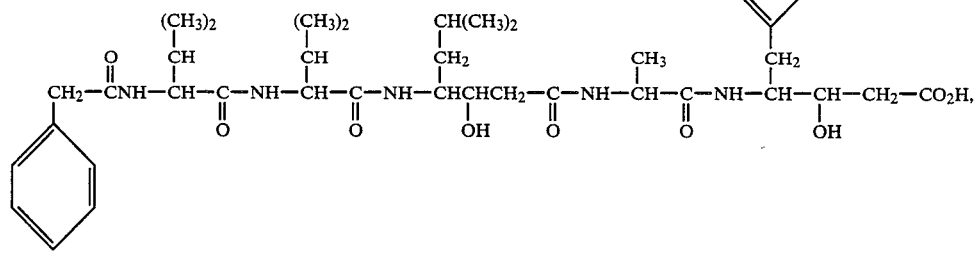

and pharmaceutically-acceptable salts thereof.

Pharmaceutically-acceptable salts of the Formula I compound include acid addition salts, such as acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, amleate, methanesulfonate, 2-naphthalenesulfonate, nicotinate, oxalate, pamoate, pectinate, persulfate, 3-phenylpropionate, picrate, pivalate, propionate, succinate, tartrate, thicyanate, tosylate, and undecanoate. The base salts of these compounds include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl and dibutyl; and diamyl sulfates or long chain halides such as decyl, lauryl, myristyl and stearyl chlorides, bromides and iodides or aralkyl halides like benzyl and phenethyl bromides and others. Conventional methods of preparing these water or oil-soluble or dispersible salts may be used.

There is further provided in the present invention a pharmaceutical composition for treating renin-associated hypertension and congestive heart failure, comprising a pharmaceutical carrier, optionally with an adjuvant, and a therapeuticaly-effective amount of the peptide of the formula I. The actual amount of active ingredient that may be combined with the carrier materials to produce a single dosage form will vary depending upon the host treated and the particular mode of administration, as determined within the professional competence of the attending physician.

The present invention also encompasses the use of the novel peptide of formula I as a starting material for the preparation of the peptide bond-isostere statine and its benzyl analog, by acid hydrolysis and chromatography.

The inhibitor/statine-starting material of the present invention may be prepared by the aerobic fermentation of a new strain of the microorganism, Streptomyces hygroscopicus (isolated from the forest soil of a small, isolated island of Japan, with a biologically-pure culture of which being maintained as Merck Culture Collection MA6044, deposited under the Budapest Treaty with the American Type Culture Collection, Rockville, Maryland, on June 8, 1987, under Accession No. ATCC 53628), or of other natural or artificial mutants or variants derived by physical or chemical mutagens (such as ultraviolet irradiation or nitrosoguanidine treatment, or recombinat techniques, such as protoplast fusion, plasmid incorporation, gene transfer, and the like) produced or derived from the Streptomyces hygroscopicus culture or of other species of the genus, Streptomyces, capable of producing the desired inhibitor compound.

The cultural characteristics of the producing organism were compared with culture descriptions of other Streptomyces species described in Bergey's Manual of Determinative Bacteriology, Eighth Edition, 1974, Williams & Wilkens, Baltimore, MD, and the Intenational Streptomyces Project reports: Shirling, E. B.& D. Gottlieb, "Cooperative description of type cultures o f Streptomyces, II. Species description from first study", Intern. J. Syst. Bateriol. (IJSB) 18: 69 189, 1968;"III. Additional species descriptions from first and second studies", IJSB 18: 279 392, 1968;"IV. Species descriptions from the second, third, and fourth studies", IJSB, 19: 391 512, 1969;"V. Additional descriptions", IJSB 22: 265 394, 1972. By this method, the producing organism was identified as a new strain of the known species, Streptomyces hygroscopicus.

The cultural characteristics of this new strain of Streptomyces hygroscopicus (where V = vegetative growth; A = aerial mycelium; and SP = soluble pigment; and all readings were taken after three weeks at 18° C., unless noted otherwise, with the pH of all media approximately neutral [6.8–7.2]) include:

Morphology: Sporophores form short compact spirals clustered along the aerial hyphae, and as the culture ages, these spores coalesce to form large moist clusters.

Yeast extract-malt extract agar (ISP Medium 2)
V: Reverse - grayish-tan
A: Flat, granular, gray mixed with much white, giving speckled salt/pepper appearance, edged with dk gray
SP: None Oatmeal agar (ISP Medium 3)
V: Reverse - dark gray
A: Flat, granular, dark gray mixed with some white
SP: None Inorganic salts-starch agar (ISP Medium 4)
V: Reverse - dark gray
A: Flat, granular, dark gray, becoming moist as culture ages
SP: None shows hydrolysis of starch Glycerol asparagine agar (ISP Medium 5)

V: Reverse - dark gray
A: Med. gray mixed with some white, edged in dark gray, flat, granular
SP: None
Peptone-iron-yeast extract agar (ISP Medium 6)
V: Grayish tan
A: None
SP: None
Melanin: Negative
Tyrosine agar (ISP Medium 7)
V: Reverse - grayish tan
A: Light gray mixed with some white, edged with dark gray
SP: None
Czapek-dox agar
V: Reverse - tan
A: Grayish-white, flat, granular
SP: None
Egg albumin agar
V: Reverse - grayish tan
A: Med. gray mixed with white, edged with dark gray, flat, granular
SP: None
Carbon Utilization
Pridham-Gottlieb basal medium (ISP Medium 9)+1% carbon source; +=growth; ±=growth poor or questionable; −−=no growth as compared to negative control (no carbon source)
  Glucose: +
  Arabinose: +
  Cellulose: −
  Fructose: +
  Inositol: +
  Lactose: ±
  Maltose: +
  Mannitol: +
  Mannose: +
  Raffinose: +
  Rhamnose: −
  Sucrose: +
  Xylose: +
  Temperature range (Yeast extract-dextrose+salts agar)
  28° C. - Good growth and sporulation
  37° C. - Poor vegatative growth - no aerial hyphi
  42° C. - No growth
  50° C. - No growth
Oxygen requirements (Stab culture in yeast extract-dextrose +salts agar)
  Aerobic The controlled aerobic fermentation of this new strain of *Streptomyces hygroscopius* is conducted in a suitable nutrient media which contains sources of assimilable carbon (such as from any of a wide variety of carbohydrates, including glucose, fructose, maltose, sucrose, xylose, and the like), especially in the presence of nitrogen sources, including proteinaceous materials (such as yeast hydrolysates, primary yeast, soybean meal, hydrolysates of casein, distillers solubles, corn-steep liquor, tomato paste, amino acids, figs, malts, cottonseed flour, lard water, animal viscera, and the like) and nutrient inorganic salts (such as the customary salts capable of yielding sodium, calcium, potassium, cobalt, manganese, iron, magnesium, ammonium, phosphate, sulfate, chloride, carbonate, and the like) at temperatures ranging from about 24° to 32° C., optimally at about 28° C., in a pH controlled to 6.8–7.4 by the use of suitable organic buffers incorporated into the fermentation medium. Any of a wide variety of media which contain at least carbon and nitrogen sources (preferably in a ratio of nutritional nitrogen sources to nutritional carbon sources of from 1:2 to 2:1, particularly in a ratio of from 0.8 to 1.2), with optional additional nutrients supplied by mineral salts and trace metals, may be used.

The inoculum for the fermentation may come from a small aliquot (seed) of vegetative growth in a seed medium which supports rapid growth of the microorganism or directly from spores, which is then innoculated into a production medium for large scale fermentation under optimum conditions. Usually the maximum yield of the inhibitor is achieved within about 24 to 200 hours, particularly in from 24 to 36 hours, although variations in the medium or in the microorganism will alter the rate of production and/or its yield. The accumulated products of the fermentation may then be separated and recovered from the broth by conventional chromatographic means.

Such a separation might include filtration of the fermentation broth to separate mycelia from liquid supernatant. The supernatant is shaken with an equal volume of a moderately polar, water-immiscible solvent, such as chloroform, ethyl acetate, methyl ethyl ketone, and the like, and the layers are allowed to settle. The mycelia are stirred vigorously (homogenized) with several volumes of solvents, such as acetone, ethyl acetate, methyl ethyl ketone, or the like, which will dissolve most of the pepstatin phenyl derivatives located within the mycelia. The combined mycelia and supernatant organic extracts are concentrated to a small volume under reduced pressure. The resultant mass is subjected to a series of solvent partioning and washing steps, using petroleum ether, hexane, ether, methylene chloride, methanol and similar solvents.

Adsorption and partition chromatograhies, gel filtration, reversed-phase liquid chromatography and the like may be used, in conjunction with eluents of proper polarity and solubilizing characteristics to afford the desired pepstatin phenyl derivative.

The novel peptide of the present invention possesses a high degree of activity in treating renin-associated hypertension and congestive heart failure in humans, as well as in other warm-blooded animals, such as mice, rats, horses, dogs, cats, etc.

Therefore, in accordance with the present invention there is still further provided a method of treating renin-associated hypertension and congestive heart failure, comprising administering to a patient in need of such treatment, a therapeutically-effective amount of a peptide of the formula I.

For these purposes, the peptide of the present invention may be administered orally, parenterally (including subcutaneous injections, intravenous, intramuscular, intrasternal injection or infusion techniques), by inhalation spray, or rectally in dosage unit formulations containing conventional non-toxic pharmaceutically-acceptable carriers, excipients, adjuvants and other vehicles.

The pharmaceutical compositions may be in the form of a sterile injectable preparation, for example, as a sterile injectable aqueous or oleagenous suspension. This suspension may be formulated according to the known art using suitable dispersing or wetting agents and suspending agents. The sterile injectable preparation may also be a sterile injectable solution or suspension in a non-toxic parenterally-acceptable diluent or solvent, for example, as a solution in 1,3-butanediol.

Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The peptides of this invention may also be administered in the form of suppositories for rectal administration of the drug. These compositions can be prepared by mixing the drug with a suitable nonirritationg excipient, such as coca butter or polyethylene glycol, which is solid at ordinary temperatures by liquid at the rectal temperature and will therefore melt in the rectum to release the drug.

Dosage levels of the order of 0.1 to 4.0 grams per day parenterally are useful in the treatment of the above indicated conditions, with oral doses three-to-ten times higher. For example, renin-associated hypertension and hyperaldosteronism are effectively treated parenterally by the administration of from 1.0 to 50 milligram of the compound per kilogram of body weight per day. It will be understood, however, that the specific dose level for any particular patient will depend upon a variety of factors, including the activity of the specific compound employed, the age, body weight, general health, sex, diet, time of administration, route of administration, rate of excretion, drug combination and the severity of the particular condition undergoing therapy.

The renin-inhibitory peptides of the present invention may also be utilized as diagnostic methods for the purpose of establishing the significance of renin as a causative of contributory factor in hypertension or congestive heart failure in a particular patient.

Both in vivo and in vitro methods may be employed. In the in vivo method, a novel peptide of the present invention is administered to a patient. in a single dose of from 0.1 to 10 mg per kg of body weight, preferably by intravenous injection, although other routes of parenteral administration are also suitable, at a hypotensive dosage level and as a single dose, and there may result a transitory fall in blood pressure. This fall in blood pressure, if it occurs, then indicates supranormal plasma renin levels.

The following Examples are intended to be representative and not limiting.

EXAMPLE 1

A frozen spore stock of the culture ATCC (Merck Culture Collection MA6044) was prepared by suspending the contents of a lyophilized preparation in 1 ml of sterile distilled water and applying its content to the surface of several BYME agar plates.

| BYME Agar | |
|---|---|
| Yeast Extract (Difco) | 4.0 g/L |
| Malt Extract (Difco) | 10.0 g/L |
| Glucose | 4.0 g/L |
| 3-N-(Morpholino)-propane-sulfonic acid | 5.8 g/L |
| pH 7.2 | |

These plates were incubated at 28° C. for 10-14 days, with the resulting spores being harvested and suspended in buffered 0.5% methylcellulose, prior to freezing at −80° C.

A frozen vial containing the spores o f the culture MA6044 was thawed and 0.1 ml of its contents used ot inoculate a 250 ml baffled flask containing 50 ml of KE medium.

| KE | |
|---|---|
| Glucose | 1.0 g/L |
| Dextrin | 10.0 g/L |
| Beef Extract | 3.0 g/L |
| Ardamine pH | 5.0 g/L |
| NZ Amine ε | 5.0 g/L |
| $MgSO_4 \cdot 7H_2O$ | 0.05 g/L |
| Phosphate Buffer | 2.0 ml |
| $CaCO_3$ | 0.5 g/L |
| pH 7.0-7.2 | |

| Phosphate Buffer | |
|---|---|
| $K_2HPO_4$ | 91.0 g/L |
| $Na_2HPO_4$ | 95.0 g/L |
| pH 7.0 | |

This seed was incubated at 28° C. for 2 days at 220 rpm.

A 2% seed inoculum was then used to inoculate a 3 L stirred fermentation vessel containing R2 medium

| R2 | |
|---|---|
| Glucose | 19.0 g/L |
| Yeast Extract (Difco) | 7.0 g/L |
| Edamine (Sheffield) | 7.0 g/L |
| Amisoy (Sheffield) | 7.0 g/L |
| Malt extract (Difco) | 6.0 g/L |
| $NaH_2PO_4$ | 1.4 g/L |
| N—2-hydroxyethylpiperazine-N'—2-ethanesulfonic acid | 13.0 g/L |
| pH 7.0 | | in which sterile glucose had been added after the medium was sterilized by steam treatment. The vessel was kept at 28° C. and stirred at 500 rpm, with 0.75 L/min air flow for 48 hours, with the remainder of the fermentation period being at 700 rpm, with 1.25 L/min air flow.

The inhibitor prepared according to this procedure demonstrated 97% renin inhibition, at a 1:10 dilution with 50% methanol, within 32 hours; and the titer remained at 91-100% inhibition throughout the remaining incubation period.

EXAMPLE 2

A frozen vial containing the spores of Merck Culture Collection MA6044 was thawed and 0.1 ml of its contents used ot incoculate a 250 ml baffled flask containing 50 ml of R2 medium. This medium was incubated at 28° C. for 4 days at 220 rpm and at the end of the incubation period the broths were placed into a equal volume of methanol and centrifuged prior to assay. All samples were diluted with 50% methanol to determine titer endpoint.

Samples produced according to this procedure exhibited 90% renin inhibition at a 1:4 dilution.

EXAMPLE 3

Forty liters of whole broth were acidified with concentrated hydrochloric acid to pH 2.8 and extracted twice with 12 liters of ethyl acetate. The combined soluble extracts were concentrated in vacuo to dryness, and the residue was washed with hexane and redissolved in methanol.

The methanol solution was again concentrated to dryness and the residue again redissolved in methanol at 102.4 mg/ml then diluted with water to 12.5 ml (pH 2.8) and extracted sequentially with 100 ml of hexane twice, with 100 ml of methylene chloride twice and 100 ml of ethyl acetate three times. The combined ethyl acetate extracts were dried over sodium sulfate, filtered and dried in a vacuum.

The residue was redissolved in methanol to about 50 ml, with 35 mg residue/ml, and the solution was passed through an LH-20 column and the active fraction eluted with 10:1 ethyle acetate/MeOH. This fraction was then pooled and further purified by Zorbax reverse phase $C_{18}$ high performance liquid chromatography, with the active fraction from the Zorbx column being eluted with 42.5% acetonitrile/0.2% acetic acid, collected and dried.

The yield of the purified component was 4.6 mg.

Employing low resolution mass spectra and high resolution mass measurements recorded on a Finnigan-MAT212 mass spectrometer in the electron impact mode (EI, 90 eV) and positive Fast Atom Bombardment [(+)FAB] spectra obtained on a MAT731 mass spectrometer, as well as a $^1$H-NMR spectrum recorded at room temperature on a Varian XL-400 NMR spectrometer in $CD_3OD$, and comparing the resulting spectral data to those of known pepstatins, a compound of Formula I was identified as that purified component.

EXAMPLE 4

The compound of Example 1 was evaluated against renin, employing a solid phase radioimmunoassay adapted and modified from the assay of Ikedo et al., *W. of Clinical Endocrinology and Metabolism*, 54, 423–428, 1982), and pepsin assays as illustrated below:

A. Renin Assay Methodology Ten μl of the test inhibitor/broth extract from Example 1 was mixed with 5 μl of 0.11M phenylmethylsulfonyl fluoride and 0.25 ml of 0.1M potassium phosphate buffer, pH 7.0, containing 0.05% sodium azide and one mg/ml of bovine serum albumin. Twenty μl of 2 μg renin enzyme prepared from hog kidney was added and the mixture was incubated at 37° C. for 20 minutes. The enzyme reaction was initiated by adding 20 μl of substrate solution which was prepared by dissolving 4 mg of angiotensinogen in 4 ml of 0.1M potassium phosphate buffer, pH 7.0, containing 0.05% sodium azide and 1 mg/ml of BSA.

After 20 minutes incubation at 37° C., the enzyme reaction was stopped by the addition of 100μl of $^{125}$I-angiotension I tracer-pepstatin. A solution which was prepared by mixing 10 μl of 0.5 mg $^{125}$I-angiotensin I containing 200 μl of 16 mg/ml of pepstatin A in dimethyl formamide and eight ml of 0.1M potassium phosphate buffer, pH 7.0, and 0.05% sodium azide. One antibody coated ball was then added to each assay tube and the tube was vortexed and incubated at room temperature for 3 hours. Two ml of water was then added ot each tube and the solution was aspirated, with the tube with the ball being counted in a γ-counter.

The activity of the test compound was calculated based on the standard curve of known amount of angiotensin I.

BN *Pepsin Assay Methodology* Seventy-five μl of 50% aqueous MeOH extract of the test broths/inhibitor from Example 1, by 0.4 ml of 0.06N HCl and 25 μl of 0.15 μg pepsin was added ot a test tube, mixed and incubated at 37° C. for 10 minutes. The enzyme reaction was initiated by adding 0.5 ml of $^{14}$C-hemoglobin substrate containing 0.2 mg of hemoglobin and 0.003 μg of $^{14}$C-methemoglobin.

After 45 minutes incubation at 37° C., 0.1 ml of 2% hemoglobin in 0.6N HCl was added to the above solution and the enzyme reaction was stopped by adding 0.5 ml of 10% trichloroacetic acid. The tube was mixed and centrifuged for 5 minutes at 500 xg. One ml of supernatant was mixed with 10 ml of scintillation fluid and the radioactivity was counted.

The activity for the test compound was calculated by the percentage of $^{14}$C-hemoglobin being solubilized.

C. *Test Results and Analysis* The compound of Example 1 shows a dose-related inhibition against both enzymes. The $I_{50}$ for the compound of Example 1 in renin was estimated to be 70 ng/ml which is about four times more potent than that of pepstatin A. The $I_{50}$ for the compound of Example 1 in pepsin was estimated to be 0.56 ng/ml which is about one-half of the activity of pepstatin A.

Thus, the $I_{50}$ ratios of both compounds against renin and pepsin assays are summarized below:

|  | $I_{50}$ ratio of renin/pepsin |
|---|---|
| Compound of Example 1 | 125 |
| Pepstatin A | 1160 |

The $I_{50}$ ration of the compound of Example 1 is about ten times better than that of pepstatin A.

What is claimed is:

1. A compound of the formula or a pharmaceutically-acceptable salt thereof.

2. A composition comprising a therapeutically-effective amount for treating renin-associated hypertension or congestive heart failure of a compound according to claim 1, and a pharmaceutical carrier.

3. A composition according to claim 2 also comprising an adjuvant.

4. A method of treating renin-associated hypertension or renin-associated congestive heart failure comprising administering to a patient in need of such treatment, a therapeutically-effective amount of the compound according to claim 1.

5. A method according to claim 4, wherein the therapeutically-effective amount is from 0.1 to 4.0 gm/day.

6. A method of identifying renin as a causative factor in patients suffering from hypertension comprising administering to such a patient between 0.1 and 10 mg of body weight of a compound according to claim 1 and measuring the fall in blood pressure of said patient.

* * * * *